United States Patent
Zhong et al.

(10) Patent No.: US 12,144,789 B2
(45) Date of Patent: Nov. 19, 2024

(54) PHARMACEUTICAL COMPOSITION EXHIBITING ANTI-TUMOR ACTIVITY, METHOD FOR TREATING PATIENT SUFFERING FROM CANCER AND METHOD FOR INHIBITING TUMOR GROWTH

(71) Applicant: Gongwin Biopharm Co., Ltd., Taipei (TW)

(72) Inventors: Nanshan Zhong, Guangzhou (CN); Longjiang Li, Chengdu (CN); Chia-Shun Shih, Taipei (TW); Lester J. Wu, Cape Coral, FL (US); Mao-Yuan Lin, Taipei (TW)

(73) Assignee: Gongwin Biopharm Co., Ltd., Taipei (TW)

( * ) Notice: Subject to any disclaimer, the term of this patent is extended or adjusted under 35 U.S.C. 154(b) by 289 days.

(21) Appl. No.: 17/579,013

(22) Filed: Jan. 19, 2022

(65) Prior Publication Data

US 2022/0133661 A1      May 5, 2022

Related U.S. Application Data

(63) Continuation of application No. 15/245,170, filed on Aug. 23, 2016, now abandoned.

(51) Int. Cl.
  *A61K 31/18*   (2006.01)
  *A61K 9/08*    (2006.01)
  *A61K 47/10*   (2017.01)

(52) U.S. Cl.
  CPC ............... *A61K 31/18* (2013.01); *A61K 9/08* (2013.01); *A61K 47/10* (2013.01)

(58) Field of Classification Search
  CPC ..................................................... A61K 31/18
  See application file for complete search history.

(56) References Cited

U.S. PATENT DOCUMENTS 5,891,454 A    4/1999  Wu
6,727,287 B2   4/2004  Wu

FOREIGN PATENT DOCUMENTS

| CN | 1073415 | 10/2001 |
| CN | 102389410 | 3/2012 |
| CN | 104473914 | 4/2015 |

OTHER PUBLICATIONS

Liu et al., Para-toluenesulfonamide induces tongue squamous cell carcinoma cell death through disturbing lysosomal stability, 2015 Wolters Kluwer Health, Inc., Jul. 23, 2015, Anti-Cancer Drugs 2015, vol. 26, No. 10, p. 1026-1033.
Naik et al. J. Gastrointestin. Liver Dis., 2009, vol. 18, No. 4, pp. 487-489 (Year: 2009).
Neidle, Cancer Drug Design and Discovery, Elsevier/Academic Press, 2008, pp. 427-431 (Year: 2008).
English translation of CN102389410A, accessed from Google Patents, Oct. 19, 2017 (Year: 2017).

*Primary Examiner* — James D. Anderson
(74) *Attorney, Agent, or Firm* — Fox Rothschild LLP

(57) ABSTRACT

A pharmaceutical composition exhibiting anti-tumor activity is provided. The pharmaceutical composition comprises para-toluenesulfonamide (PTS) and a pharmaceutically acceptable carrier. The pharmaceutical composition is used for treating squamous-cell carcinoma. The present invention further provides a method for treating a patient suffering from cancer and a method for inhibiting tumor growth.

14 Claims, 11 Drawing Sheets

Control

PTS

PHARMACEUTICAL COMPOSITION EXHIBITING ANTI-TUMOR ACTIVITY, METHOD FOR TREATING PATIENT SUFFERING FROM CANCER AND METHOD FOR INHIBITING TUMOR GROWTH

CROSS REFERENCE TO RELATED APPLICATIONS

This application is a continuation application of U.S. patent application Ser. No. 15/245,170 filed on Aug. 23, 2016. The entire contents of the application are incorporated herein by reference in their entirety.

BACKGROUND OF THE INVENTION

1. Field of the Invention

The present invention is related to a pharmaceutical composition exhibiting anti-tumor activity, a method for treating a patient suffering from cancer and a method for inhibiting tumor growth, and more particularly, the present invention is more effective in squamous cell carcinoma.

2. Description of the Prior Art

Toluene sulfonamide is widely known as a highly effective anti-fungal agent exhibiting anti-fungal activity against fungal infected plant tissues and human skin. For instance, Harry Pugh disclosed in 1967 that para-toluene is highly effective as a topical agent for the treatment of skin fungal diseases. According to Pugh, such anti-fungal activity is achieved by incorporating para-toluene sulfonamide with propylene glycol to form a 7-8% solution by weight. The present invention relates to efficacious anti-cancer compositions that were not previously described.

SUMMARY OF THE INVENTION

According to one embodiment of the present invention, a pharmaceutical composition exhibiting anti-tumor activity is provided. The composition comprises para-toluenesulfonamide (PTS) and a pharmaceutically acceptable carrier. The pharmaceutical composition is used for treating squamous-cell carcinoma.

In another embodiment of the present invention, a method for treating a patient suffering from cancer is provided. The method comprises administering a pharmaceutical composition to a patient with squamous-cell carcinoma, wherein the pharmaceutical composition comprises PTS.

In another embodiment of the present invention, a method for inhibiting cancer cell growth is further provided. First, a target body with plural cancer cells is provided, wherein the cancer cells include squamous-cell carcinoma. Then, a composition is applied to the target body, wherein the composition comprises PTS.

The pharmaceutical composition, the method described herein can also be used to shrink a tumor in a human patient who has a tumor such as squamous cell carcinoma. The invention is further characterized in that PTS selectively triggers cancer cell apoptosis, in comparison to normal cells, through disturbing lysosomal stability and inducing mitochondrial dysfunction. The pharmaceutical composition with PTS in the present invention can exhibits potent anti-cancer activity and specificity to cancer cells without exerting side effect to normal cells.

These and other objectives of the present invention will no doubt become obvious to those of ordinary skill in the art after reading the following detailed description of the preferred embodiment that is illustrated in the various figures and drawings.

DETAILED DESCRIPTION

Figure 1A:
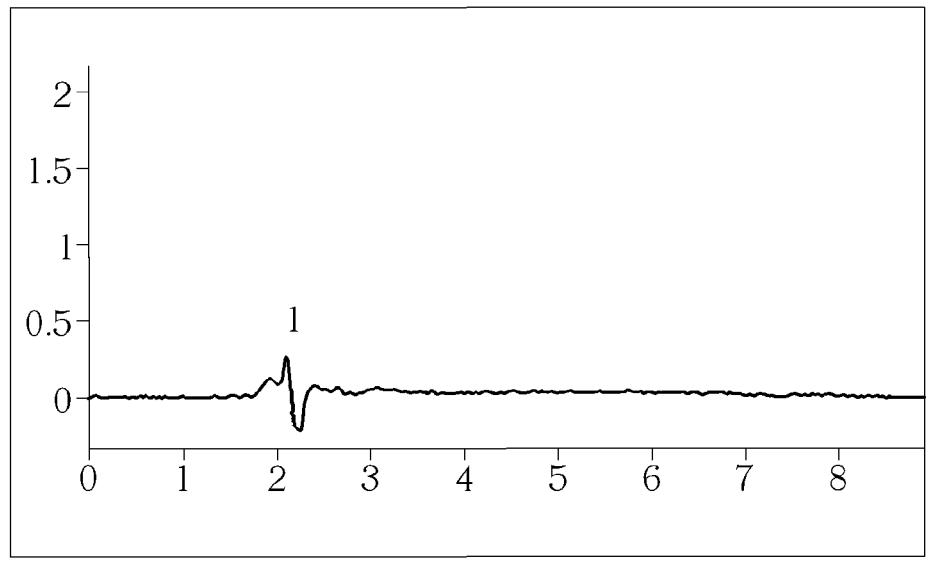
FIG. 1A and FIG. 1B show HPLC results of the intracellular contents in Tca-8113 with and without treating PTS.

To provide a better understanding of the presented invention, preferred embodiments will be described in detail. The preferred embodiments of the present invention are illustrated in the accompanying drawings with numbered elements.

The present invention is related to a pharmaceutical composition and a method of treating a human patient suffering from a cancer, which is characterized by administration to said patient with PTS and a pharmaceutically acceptable carrier. Since PTS is not readily dissolved in water or in a water-based solution, it is critical to develop a suitable formulation which will facilitate the mixing or dissolution of PTS in or with a group of solvents or surfactants. The suitable formulation may include, for example, polyethylene glycol, 2-ethyl-1,3-hexanediol, propanediol, decanedioic acid, dimethyl sulfoxide, ethanol, honey, a surfactant (i.e., other than, or in addition to, honey), and an emulsifier. Examples of suitable surfactants include honey, hexadecanol, propanediol alginate, glycerol monostearate, and xylitan monostearate. Examples of suitable emulsifiers include hexadecanol, TWEEN™ surfactants (e.g., TWEEN20™), lecithin, and other known emulsifying agents, and is not limited thereto. As used herein, the term "pharmaceutically acceptable carrier" means a chemical composition with which the active ingredient may be combined and which, following the combination, can be used to administer the active ingredient to a subject.

In one embodiment, the method includes treating a patient suffering from cancer is provided. The method comprises administering a pharmaceutical composition to a patient with a cancer, wherein the pharmaceutical composition comprises 2.5 μmol/l to 80 μmol/l of a PTS.

In another embodiment, the present invention further provides a method for inhibiting cancer cells growth. First, a target body with a cancer cell cultured therein is provided. In one embodiment, the target body can be any container that has biocompatibility for providing a space to accumulate the cancer cells for surviving. In one embodiment, the target body is a living body such as human. In another embodiment, the target body can be non-living object such as cultured dish, biological duct, but is not limited thereto. Then, a composition is applied to the target body, wherein the composition comprises 2.5 μmol/l to 80 μmol/l of a PTS, so as to suppress the cancer cells. In one embodiment, the target body further comprises plural normal cells such as fibroblasts and PTS can selectively inhibit the cancer cell without affecting the normal cells.

The term "cancer cell" is used herein to mean a transformed cell, more definitely, an animal cell which shows chromosome abnormality by G-Band nucleo analysis [M. E. Drets, et al, *Proc. Natl. Acad. Sci.*, U.S.A. (1971) 68:2073]. In the present invention contact inhibition can be used as a measure of the transformed cell, since cancer cell generally shows no contact inhibition. The contact inhibition of a cell can be judged by whether the cell proliferates or not after a confluent stage in a monolayer culture.

The term "normal cell" is used herein to mean an animal cell excluding the above described cancer cell. In other words, it refers to the animal cell which is not in a state of malignant transformation. In the present invention, fibroblast which exist in abundance in vivo and can be relatively easily isolated is the most preferred normal cell. If desired or necessary, two or more kinds of normal cells can be used. Sometimes it is possible to better simulate the surrounding structure of in vivo tumors by using two or more kinds of normal cells.

In one embodiment, a concentration of the PTS is between 2.5 μmol/l and 80 μmol/l, preferably between 10 μmol/l and 20 μmol/l, since said concentration interval can selectively target cancer cells, but exerts less effect on normal fibroblast.

In the present invention, it is demonstrated that para-toluenesulfonamide can inhibit cell death by inhibiting ATP biosynthesis. It is demonstrated that the anticancer effects of a novel agent PTS on tongue cancer cell. PTS selectively accumulated in cancer cells, with fewer poisonous effects on normal fibroblasts. PTS inhibits tumor progression by simultaneously inducing apoptosis, and necrosis and suppressing invasive ability in cancer cells. Moreover, PTS triggers cell death through disturbing lysosomal stability and inducing mitochondrial dysfunction.

The following context will show the anti-tumor effect and anti-tumor activities of the pharmaceutical compositions with PTS.

Embodiment 1

In one embodiment, the pharmaceutical composition has the composition set forth in Table 1.

TABLE 1

| Ingredient | Concentration |
|---|---|
| Para-toluene sulfonamide | 0.001% |
| Polyethylene glycol | 6.7 wt % |
| 2-ethly-1,3-hexanediol | 3.28 wt % |
| Propanediol | 1.64 wt % |
| Decanedioic acid | 0.74 |
| Dimethyl sulfoxide | 1.34 |
| Ethanol | 0.30 |
| Honey | 86.00 |

Experiment 1

Figure 1B:
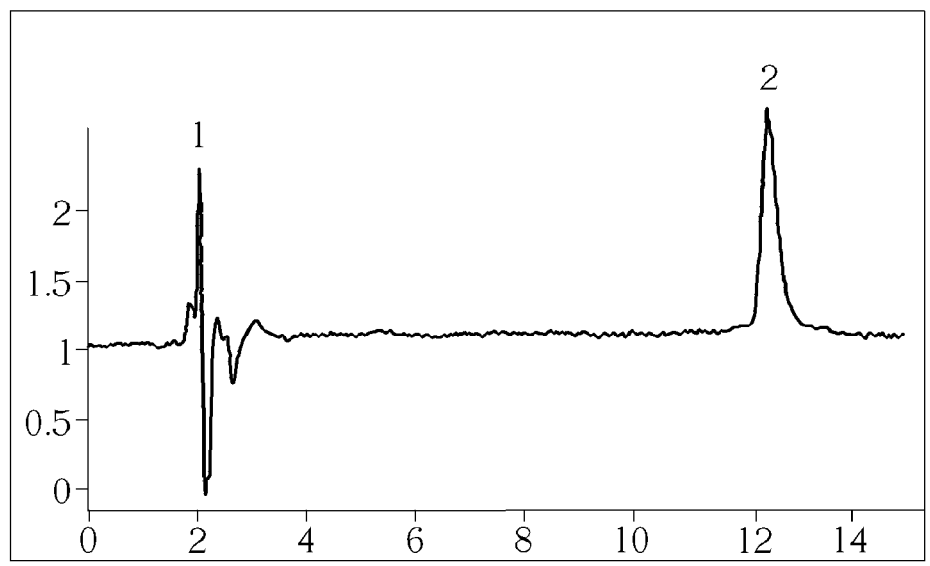

Firstly, Tca-8113 were treated with PTS or dimethyl sulfoxide (DMSO) (control vehicle) and then extract the intracellular matrix subjected to high-performance liquid chromatography. Please see FIG. 1A and FIG. 1B, which shows HPLC result with and without treating PTS in Tca-8113, wherein peak 1 represents antipyrine (internal standard) and peak 2 represents PTS. It is shown that PTS treatment can increase the intracellular PTS concentration in Tca-8113 cells in a dose dependent manner.

Figure 2A:
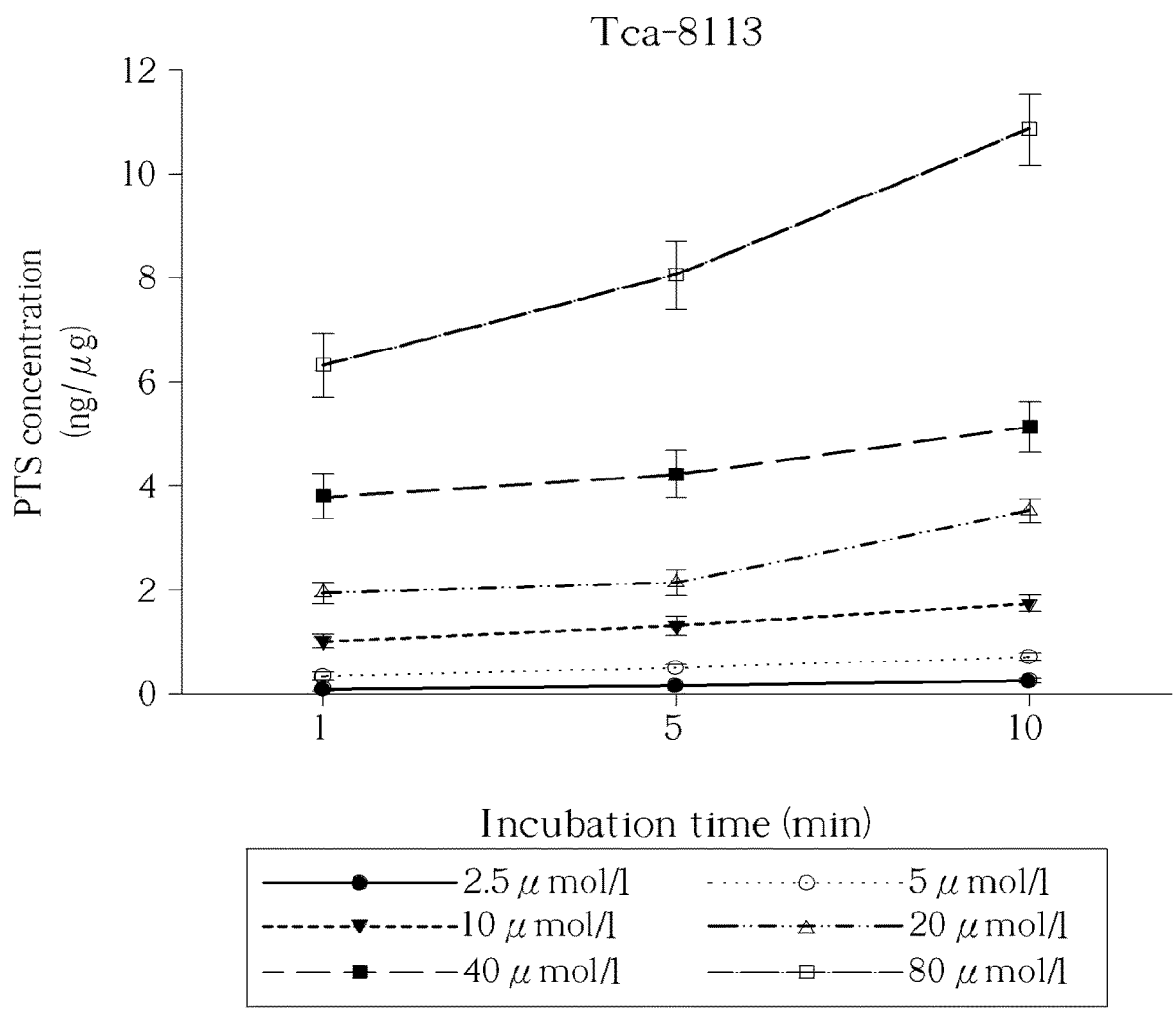
FIG. 2A and FIG. 2B show the plots of intracellular PTS concentration after 2.5 μmol/l~80 μmol/l PTS treatment for different periods of time in Tca-8113 and HGF cell, respectively.
Figure 2B:
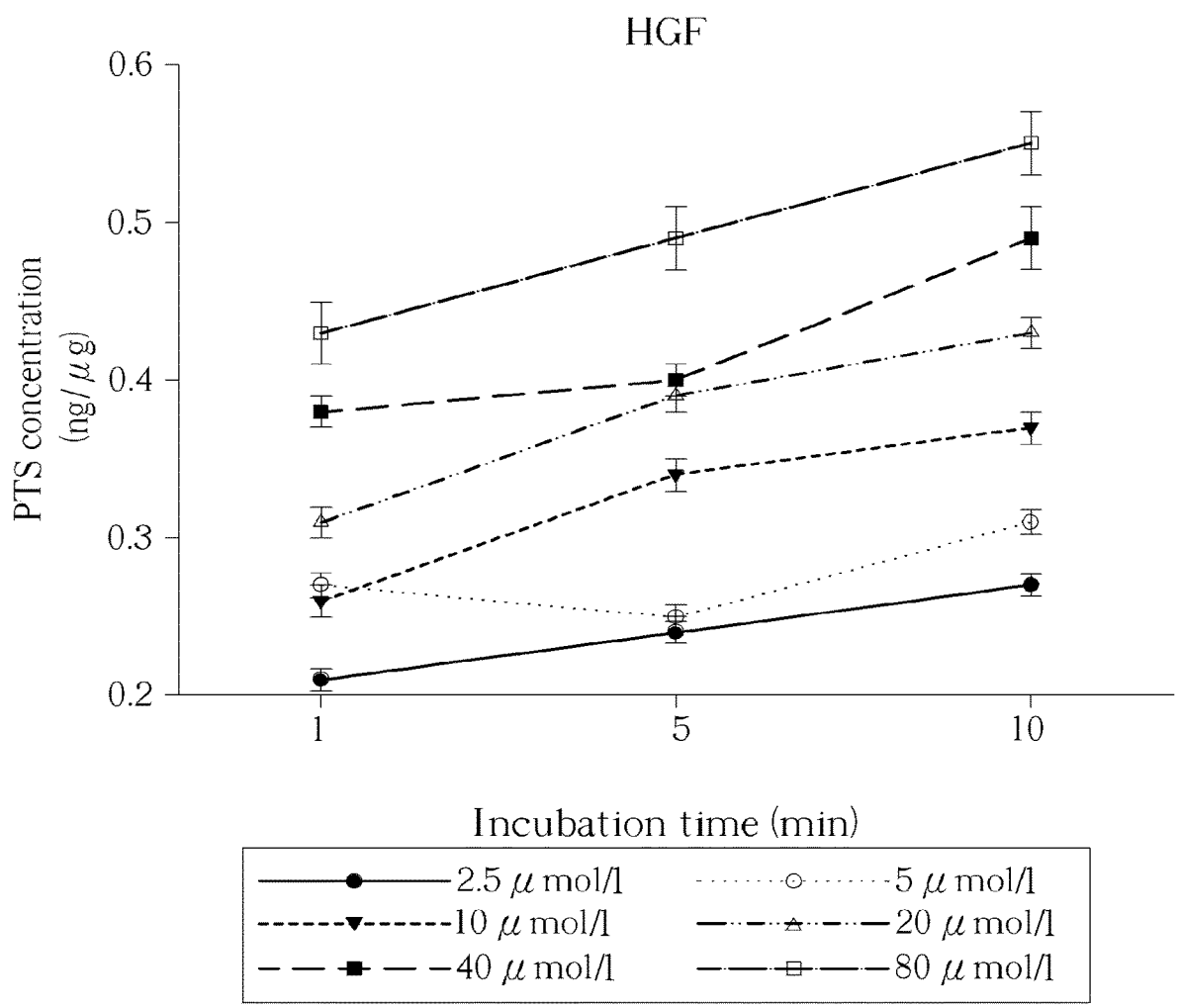
Figure 3:
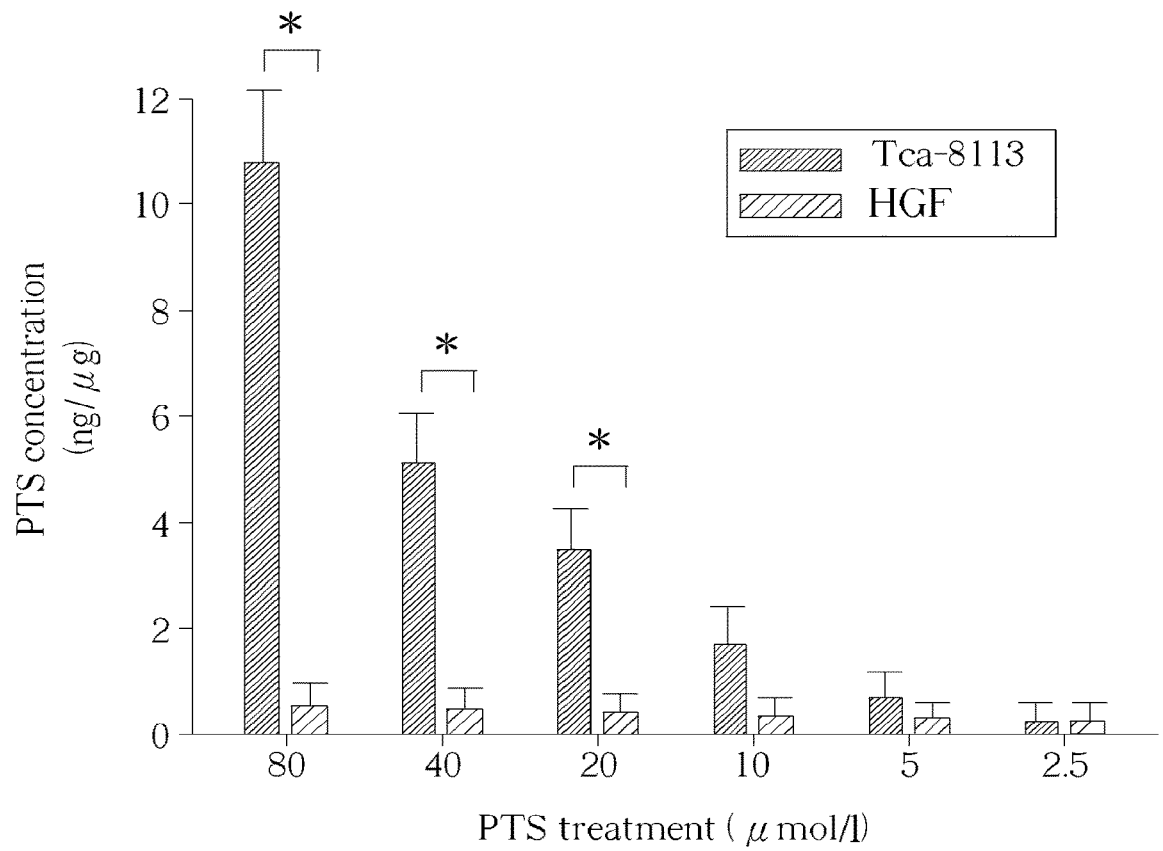
FIG. 3 shows the comparative plot of intracellular PTS concentration between Tca-8113 and HGF cell after 10 min treatment.

In assessing the accumulation of intracellular PTS between Tca-8113 cells and normal cells after different doses and incubation periods of PTS treatment, Tca-8113 and Human gingival fibroblast (HGF) cells were treated 2.5 μmol/l~80 μmol/l PTS for different periods. Please see FIG. 2A and FIG. 2B, which show the plots of intracellular PTS concentration after 2.5 μmol/l~80 μmol/l PTS treatment for different periods of time in Tca-8113 and HGF cell, respectively. As shown in FIG. 2A and FIG. 2B, increased PTS treatment significantly induced a higher level of intracellular PTS accumulation both in Tca-8113 and HGF cells. Prolonged PTS incubation also increased the intracellular PTS level. However, the accumulated intracellular PTS concentration in Tca-3118 cells is much higher than that in HGF cells. As shown in FIG. 3, after 10 min of PTS treatment, intracellular PTS accumulation was significantly inhibited in HGF cells compared with that in Tca-8113 cells under the same PTS treatment condition. The intracellular PTS concentration variation between the Tca-8113 cells and HGF cells can range from 5× (20 μmol/l), 8× (40 μmol/l) to 12 (80 μmol/l).

Experiment 1 shows that PTS selectively accumulates in Tca-8113, suggesting that PTS selectively target cancer cells, but exerts less effect on normal fibroblast.

Experiment 2

Figure 4:
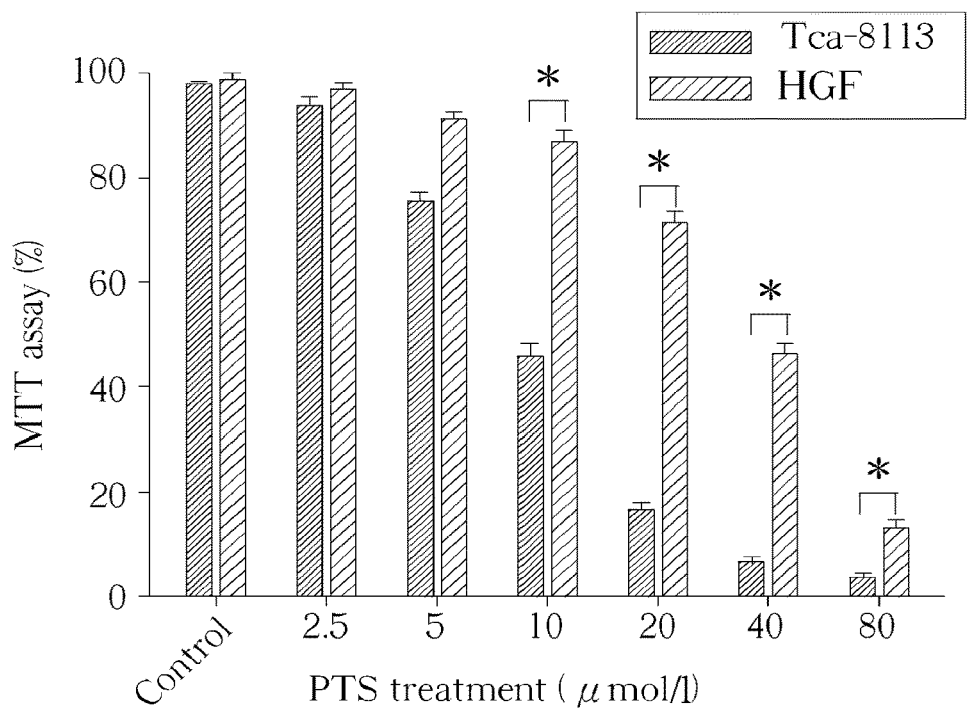
FIG. 4 shows the result of NTT assay after various concentration of PTS treatment in Tca-8113 and HGF cell.

To examine the effects of PTS on cell viability, Tca-8113 and HGF cells were treated with different doses of PTS for 1 h. The 3-(4,5-dimethylthiazol-2-yl)-2,5-diphenyltetrazolium bromide (MTT) assay is conducted by treating Tca-8113 and human gingival fibroblast (HGF) cells with 2.5 μmol/l, 5 μmol/l, 10 μmol/l, 20 μmol/l, 40 μmol/l and 80 μmol/l PTS for 1 h, respectively. The effects of PTS on cell viability were assessed using MTT 72 h after treatment. As shown in FIG. 4, PTS significantly reduced the viability of Tca-8113 cells in a dose-dependent manner wherein 80 μmol/l PTS treatment almost completely suppressed the number of viable cells. However, the inhibitory effects of PTS in HGF cells were significantly decreased compared with that in Tca-8113 cells. PTS induces more significant cell death in Tca-3118 cells than that in normal gingival fibroblasts. Taking the 10 μmol/l PBS treatment for example, about 50% Tca-8113 cells were suppressed while only 10% HGH cells were suppressed, so the suppression ratio (cancer cell suppression %/normal cell suppression %) is 5. Similarly, the suppression ratios of 20 μmol/l, 40 μmol/l and 80 μmol/l are 2.6, 1.8, 1.05. This result is consistent with the experiment 1 showing HPLC results that HGF cells accumulated less intracellular PTS.

Figure 5:
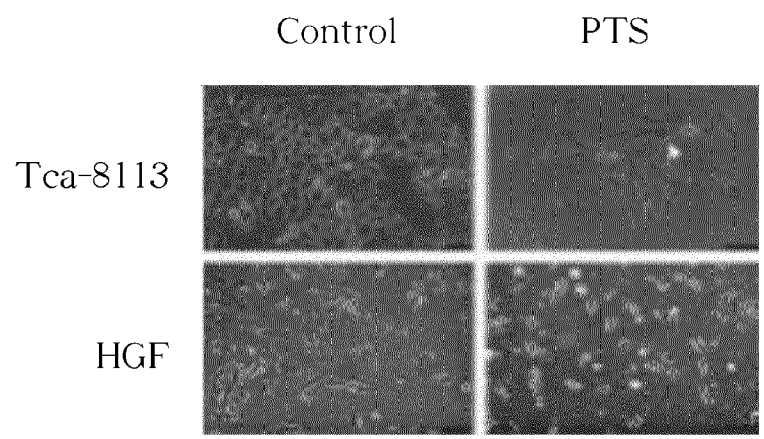
FIG. 5 shows the picture of phase-contrast microscope in control and PTS treatment of Tca-8113 and HGF cell.

Next, in observing the morphological feature of the treated cells, Tca-8113 and HGF cells were treated with 40 μmol/l PTS or DMSO (control vehicle) for 1 h; the morphologic changes were observed using a phase-contrast microscope. As shown in FIG. 5, the apoptotic body is clearly shown (arrow) (bar=30 μm), indicating 40 μmol/l PTS treatment can induce classical apoptotic features including cell shrinkage, nuclear condensation, cell density reduction, and apoptotic body formation.

Figure 6:
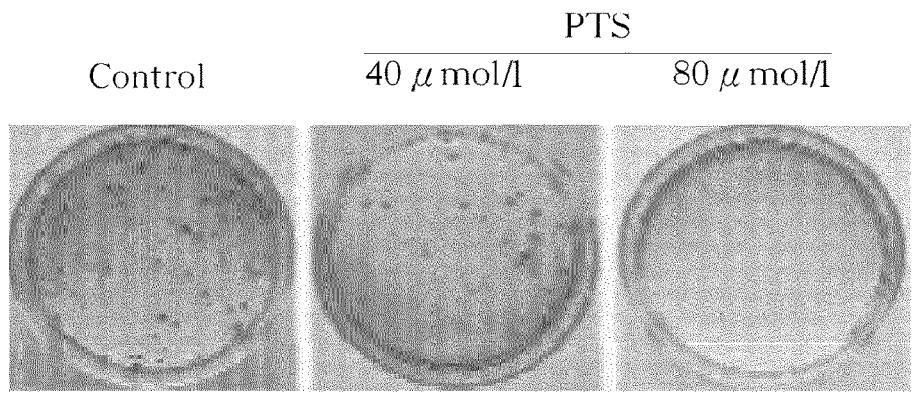
FIG. 6 shows the pictures of colony formation assay after PTS treatment in Tca8113 cell.

Colony formation assay shown in FIG. 6 further confirms the cytotoxic effects of PTS on Tca-8113 cells. As shown in FIG. 6, PTS significantly reduced the viability of Tca-8113 cells in a dose-dependent manner, wherein 80 μmol/l PTS treatment almost completely suppressed the number of viable cells. The inhibitory effects of PTS in HGF cells were significantly decreased compared with that in Tca-8113 cells, which is consistent with the HPLC results that HGF cells accumulated less intracellular PTS.

Figure 7:
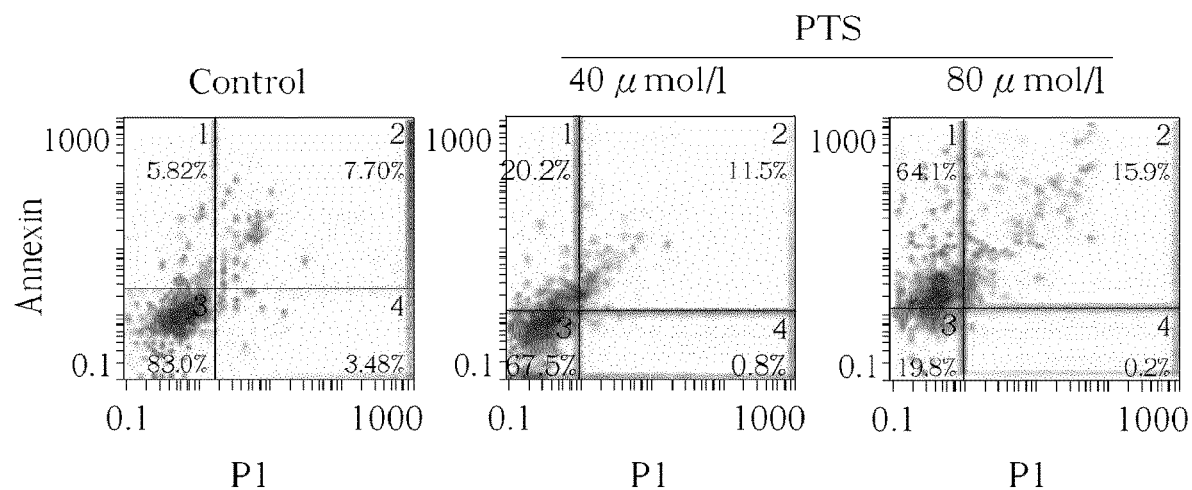
FIG. 7 shows the result of PI/Annexin V staining of flow cytometric analysis after PTS treatment in Tca-8113 cell.

Next, cancer cell death is measured by using flow cytometric analysis. Tca-8113 cells were treated with 40 μmol/l and 80 μmol/l PTS or DMSO (control) for 1 h. Cells were stained with Annexin V– FITC and propidium iodide (PI), followed by flow cytometric analysis. As shown in FIG. 7, PTS treatment for 1 hour induced a significant increase in early apoptotic rate (Annexin V+/PI–) with 5.82% (DMSO), 20.2% (40 μmol/l), and 64.1% (80 μmol/l). Late apoptotic/ necrotic rate (Annexin V+/PI+) were 7.70% (DMSO), 11.5% (40 μmol/l), and 15.9% (80 μmol/l), respectively. Viable cells (Annexin V–/PI–) decreased from 83.0% in the DMSO-treated group to 67.5 and 19.8% after 40 and 80 μmol/l PTS treatment. The results of flow cytometric analysis showed that PTS induced cancer cell death by activating apoptosis and necrosis simultaneously.

Figure 8A:
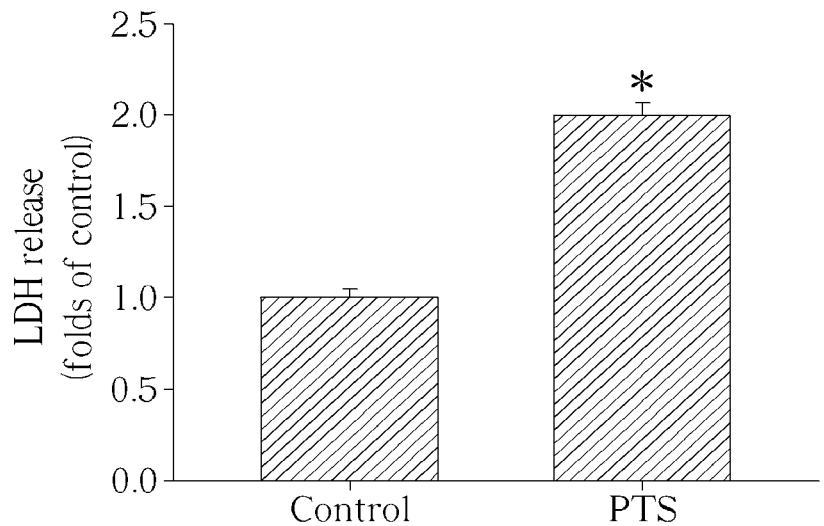
FIG. 8A and FIG. 8B show the result of LDH assay and numbers of cells migrated after PTS treatment.

Furthermore, in studying PTS-induced necrosis, LDH release assay is used. LDH is a cytosolic enzyme that can be released into culture medium upon damage of the plasma membrane. Necrosis, which results in an early loss of plasma membrane integrity, can be determined using the LDH release assay. In LDH release assay, Tca-8113 cells were treated with 80 μmol/l PTS or DMSO for 1 h; PTS-induced necrosis was determined using the lactate dehydrogenase (LDH) release assay. As shown in FIG. 8A, PTS induces a significant increase in the activity of LDH released from necrotic cells, wherein 80 μmol/l PTS treatment for 1 h induced a two-fold increase in LDH release compared with the control group.

Figure 8B:
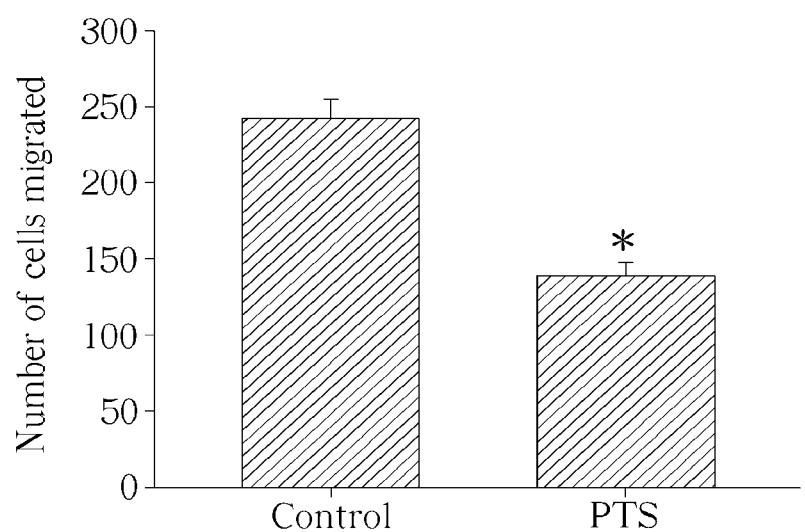

The effect of PTS on the invasive ability of cancer cells is also investigated. Tca-8113 cells were treated with 40 μmol/l PTS or DMSO for 1 h; the effects of PTS on cell migration were determined using a transwell migration assay. As shown in FIG. 8B, 40 μmol/l PTS treatment for 1 h significantly reduced the invasive ability of Tca-8113 cells.

Experiment 2 suggests that PTS activates apoptosis and necrosis simultaneously to induce cancer cell death, and inhibits the migration ability.

Experiment 3

Figure 9A:
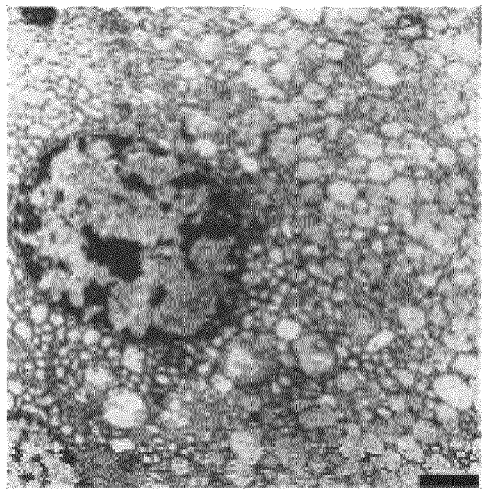
FIG. 9A and FIG. 9B show pictures of transmission electron microscope analysis in control and PTS treated Tca8113 cell.
Figure 9B:
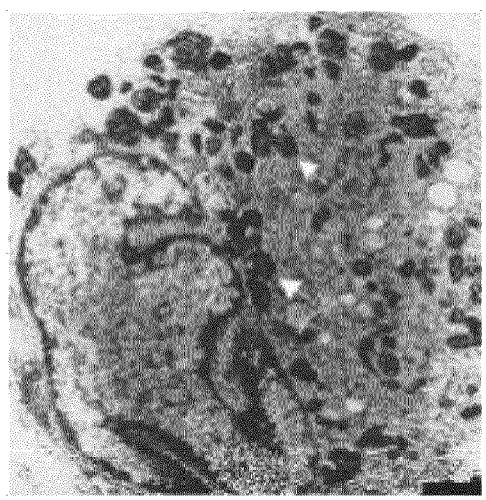

To investigate the mechanisms of PTS-induced cell death, the present invention uses transmission electron microscopy analysis to observe the changes in ultrastructures of Tca-8113 cells. Tca-8113 cells were treated with 40 μmol/l PTS or dimethyl sulfoxide for 1 h. The ultrastructural changes were observed using a transmission electron microscope. As shown in FIG. 9A and FIG. 9B, in comparison to the control treatment, cells showed shrunk nuclei and an irregular nuclear membrane after 40 μmol/l PTS treatment. More secondary lysosomes (pointed by arrow) with high electron density were observed after PTS treatment. Lysosomal instability was proposed to control the fate of cells either through activation of apoptosis or necrosis.

Figure 10:
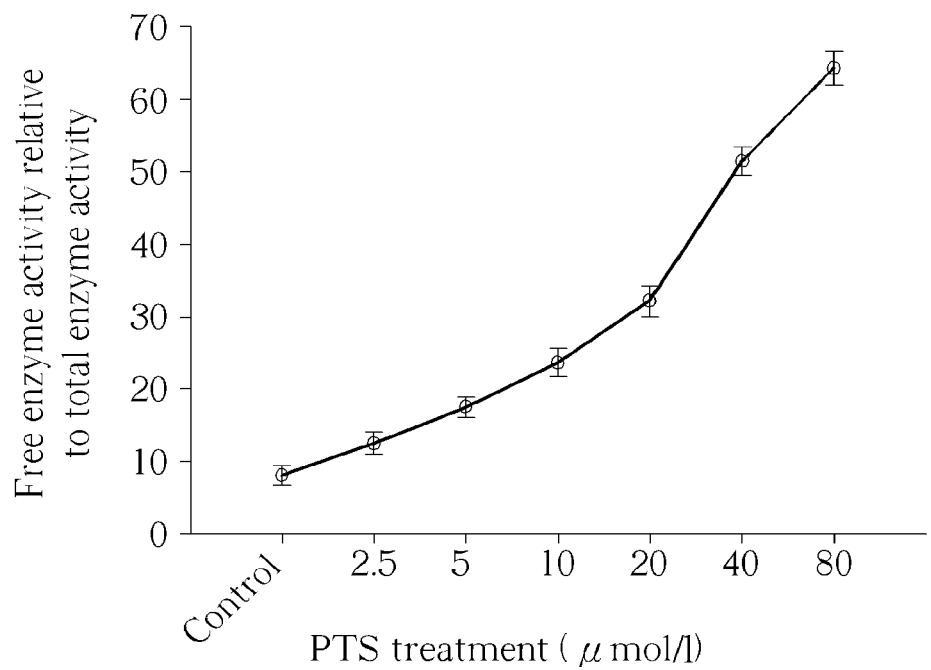
FIG. 10 shows the result of lysosomal integrity assay (LMP) after PTS treatment.

Next, a lysosomal integrity assay (LMP) is performed to assess the effects of PTS on lysosomal membrane integrity. Lysosomes of Tca-8113 cells were isolated using the Percoll gradient centrifugation method. The effects of PTS on lysosomal integrity were assessed by measuring the activity of lysosomal β-galactosidase using UMBG (4-methylumbelliferyl-β-D-galactoside). The 4-methylumbelliferone released was determined by measuring its fluorescence (excitation: 365 nm, emission: 444 nm) on a fluorescence spectrophotometer. The activity of the enzyme measured in the presence and absence of 0.36% Triton X-100 was designated the free activity and the total activity, respectively. As shown in FIG. 10, PTS was shown to significantly increase free enzyme activity in a dose-dependent manner, which suggests that PTS induces lysosomal membrane permeabilization (LMP) and lysosomal damage. LMP leads to release intra lysosomal membrane protease such as cathepsin B and D and chymotrypsin B, which are suggested to be essential downstream effectors of capases.

Figure 11A:
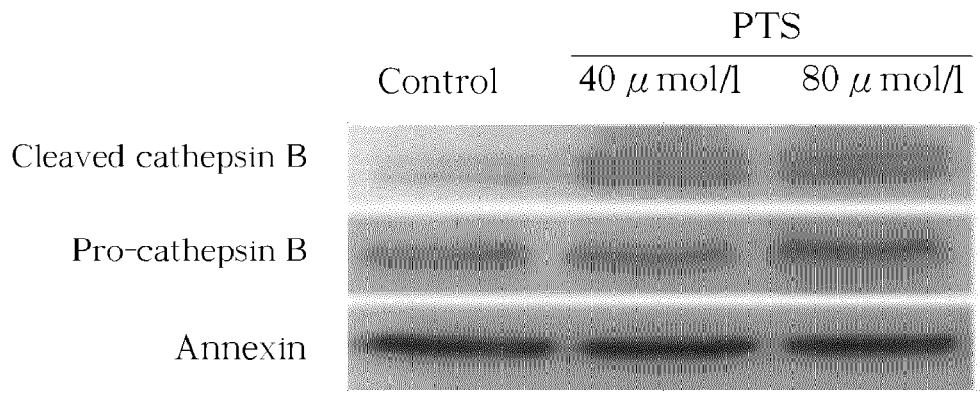
FIG. 11A shows the expression of cathepsin B of Tca-8113 cells after 40 μmol/l PTS treatment with western blot analysis for 1 h.

In the western blot analysis, Tca-8113 cells are analyzed after 40 μmol/l PTS treatment for 1 h. As shown in FIG. 11A, PTS treatment significantly increases cleaved cathepsin B expression.

Experiment 3 suggests that the anticancer ability of PTS might be attributed to inducing lysosomal instability and activating lysosomal instability, and activating lysosome mediated cell death.

Experiment 4

Figure 11B:
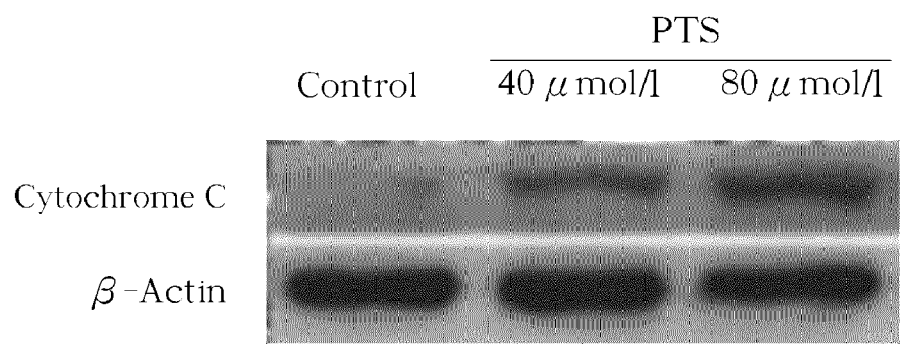
FIG. 11B shows the expression of cytochrome C of Tca-8113 cells after 40 μmol/l PTS treatment with western blot analysis for 1 h.
Figure 12:
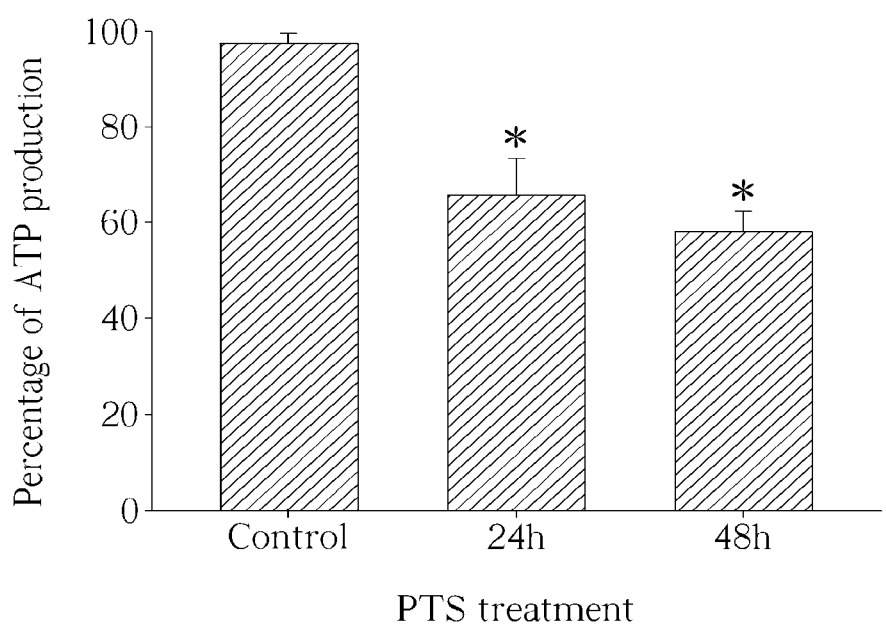
FIG. 12 shows the result of ATP synthesis percentage after PTS treatment.

Increased lysosomal permeability is reported to induce mitochondrial damage and the release of pro-apoptotic factors. The applicant therefore investigated the cytosolic cytochrome c released from the mitochondria after PTS treatment. As shown in Western blot analysis in FIG. 11B, 40 μmol/l and 80 μmol/l PTS treatment for 1 h significantly induced cytosolic cytochrome c expression in Tca-8113 cells. As the mitochondria are at the core of cellular energy metabolism and also the major organelles for ATP generation, the applicant then prove if PTS can regulate mitochondrial ATP biosynthesis. Inhibition of ATP biosynthesis is observed when Tca-8113 cells were treated with 40 μmol/l PTS or DMSO for 24-48 h. The effects of PTS on ATP biosynthesis were assessed by measuring chemiluminescence. As shown in FIG. 12, PTS treatment significantly inhibited mitochondrial ATP biosynthesis in a time-dependent manner. 40 μmol/l PTS treatment for 1 h attenuated ATP biosynthesis to 65.8%.

As shown, experiment 4 clearly shows PTS can induce mitochondrial damage and exerts a metabolic arrest effect on cancer cells.

According to the experiments shown above, the present invention provides a novel agent PTS with anticancer effects, especially in tongue cancer cells. The experiments set forth in the present invention shows that PTS selectively accumulated in cancer cells, with fewer poisonous effects on human normal fibroblasts. PTS inhibits tumor progression by simultaneously inducing apoptosis and necrosis, and suppressing invasive ability in cancer cells. Moreover, our results suggest that PTS triggers cell death through disturbing lysosomal stability and inducing mitochondrial dysfunction. It is noted that since the apoptosis pathway can be found and triggered in various kinds of cancer cells. The use of PTS therefore may not be limited to squamous-cell carcinoma cell but other types of cancers, such as head and neck cancer, lung cancer, hepatic cancer, and is not limited thereto.

Besides the potent anti-cancer effect the PTS, it is another salient feature in the present invention that using PTS with 2.5 µmol/l~80 µmol/l, especially 10 µmol/l~20 µmol/l can bring to the most anti-cancer effect but least influence to the normal cells.

In summary, the pharmaceutical composition and the method described herein can also be used to shrink a tumor in a human patient who has a tumor, or to prevent tumor genesis in a human patient who does not have, or is not recognized as having, a tumor. The invention is further characterized in that PTS selectively triggers cancer cell apoptosis, in comparison to normal cells, through disturbing lysosomal stability and inducing mitochondrial dysfunction.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for selectively treating a target cancer in a target body, comprising administering to the target body a pharmaceutical composition which comprises para-toluenesulfonamide having a concentration between 10 µmol/l and 40 µmol/l and a pharmaceutically acceptable carrier, wherein the para-toluenesulfonamide has a selectivity of the target cancer and normal cells, and wherein the selectivity of the target cancer and the normal cells is determined by a suppression ratio, which is percentage of cancer cell suppression divided by percentage of normal cell suppression, and wherein the suppression ratio is from 1.8 to 5.

2. The method of claim 1, wherein the target body is a human or a fibroblast of a human.

3. The method of claim 1, wherein the target cancer is a squamous-cell carcinoma.

4. The method of claim 3, wherein the squamous-cell carcinoma is selected from the group consisting of squamous-cell carcinoma of head and neck cancer, squamous-cell carcinoma of lung cancer, squamous-cell carcinoma of hepatic cancer, and squamous-cell carcinoma of tongue.

5. The method of claim 4, wherein the target cancer is the squamous-cell carcinoma of the tongue.

6. The method of claim 4, wherein the target cancer is the squamous-cell carcinoma of the lung.

7. The method of claim 1, wherein the para-toluenesulfonamide has a concentration between 10 µmol/l and 20 µmol/l.

8. The method of claim 1, wherein the para-toluenesulfonamide induces death of the target cell by inhibiting ATP biosynthesis, apoptosis, necrosis, disturbing lysosomal stability, or inducing mitochondrial dysfunction.

9. The method of claim 1, wherein the pharmaceutical acceptable carrier comprises polyethylene glycol, 2-ethly-1,3-hexanediol, propanediol, decanedioic acid, dimethyl sulfoxide, ethanol, honey, a surfactant, an emulsifier, or any combination thereof.

10. The method of claim 1, wherein the suppression ratio is 2.6 if the concentration is 20 µmol/l.

11. The method of claim 1, wherein the suppression ratio is 1.8 if the concentration is 40 µmol/l.

12. The method of claim 1, wherein the para-toluenesulfonamide inhibits mitochondrial ATP biosynthesis in a time dependent manner.

13. The method of claim 12, wherein the para-toluenesulfonamide reduces ATP production by more than 30% within 24 hours.

14. The method of claim 13, wherein the para-toluenesulfonamide reduces ATP production by more than 40% within 48 hours.

* * * * *